United States Patent
Wu et al.

(10) Patent No.: US 9,126,058 B2
(45) Date of Patent: *Sep. 8, 2015

(54) MOUTHWASH COMPOSITION

(71) Applicant: Far Eastern New Century Corporation, Taipei (TW)

(72) Inventors: Yong-Yi Wu, Taoyuan County (TW); Chun-Yi Li, Taoyuan County (TW); Chih-Ta Lee, Taoyuan County (TW)

(73) Assignee: FAR EASTERN NEW CENTURY CORPORATION, Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 14/162,090

(22) Filed: Jan. 23, 2014

(65) Prior Publication Data

US 2014/0242002 A1 Aug. 28, 2014

(30) Foreign Application Priority Data

Feb. 23, 2013 (TW) .............................. 102106425 A

(51) Int. Cl.
*A61Q 11/00* (2006.01)
*A61Q 17/00* (2006.01)
*A61K 8/88* (2006.01)

(52) U.S. Cl.
CPC . *A61Q 11/00* (2013.01); *A61K 8/88* (2013.01); *A61Q 17/005* (2013.01)

(58) Field of Classification Search
CPC ........... A61K 2800/92; A61K 2300/00; A61Q 11/00; A61Q 17/005
USPC .......................................................... 424/49
See application file for complete search history.

(56) References Cited

U.S. PATENT DOCUMENTS

| | | | |
|---|---|---|---|
| 3,998,945 A * | 12/1976 | Vit .................................. | 424/53 |
| 4,339,431 A * | 7/1982 | Gaffar ............................ | 424/54 |
| 5,753,217 A | 5/1998 | Christopfel | |
| 2012/0082638 A1* | 4/2012 | Li et al. ...................... | 424/78.37 |

FOREIGN PATENT DOCUMENTS

| | | |
|---|---|---|
| TW | I305497 B | 1/2009 |
| TW | 201121576 A | 7/2011 |
| TW | 201215318 A | 4/2012 |

OTHER PUBLICATIONS

J. Tonzetich et al., "Evaluation of volatile odoriferous components of saliva" Archives of Oral Biology, vol. 9, Issue 1, pp. 39-45, Jan.-Feb. 1964.

Mel Rosenberg, "The Science of Bad Breath", Scientific American, p. 72-78, Apr. 2002 (English and Chinese versions).

* cited by examiner

*Primary Examiner* — Frederick Krass
*Assistant Examiner* — Tracy Liu
(74) *Attorney, Agent, or Firm* — Rabin & Berdo, P.C.

(57) ABSTRACT

A mouthwash composition comprises water and a modified polyglutamic acid composed of a plurality of segment A and a plurality of segment B randomly arranged, in which, the segment A has a formula I:

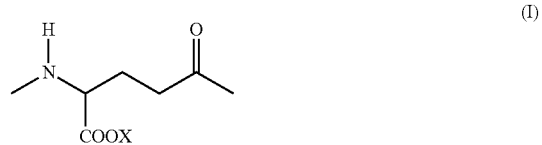

The segment B has a formula II:

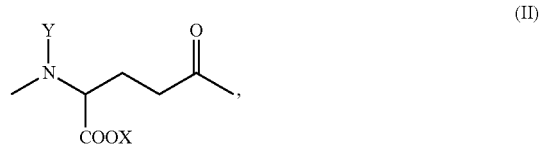

wherein X=H, Na, K, $NH_4$, ½Ca, or ½Mg, and Y=Cl, Br, or I. The modified polyglutamic acid in the mouthwash composition is 0.1-5 wt %. The mouthwash composition in the present invention can eliminate bad breath, and also has antibacterial properties, so it can suppress the formation of dental plaque and is effective in preventing periodontal disease.

11 Claims, No Drawings

MOUTHWASH COMPOSITION

RELATED APPLICATIONS

This application claims priority to Taiwanese Application Serial Number 102106425, filed Feb. 23, 2013, which is herein incorporated by reference.

BACKGROUND

1. Field of Invention

The present invention relates to a mouthwash composition. More particularly, the present invention relates to a mouthwash composition that can eliminate bad breath and prevent periodontal disease.

2. Description of Related Art

The bad breath is one of the problems to be avoided most for people who need to have face-to-face contact with others. Severe bad breath will affect social relation and activities of individuals.

Bad breath mainly comes from undesirable smells emitting by the volatile compounds in mouth, e.g. volatile sulfides, short-chain fatty acids, polyamines, alcohols, phenols, alkanes, ketones, and nitrides. In particular, volatile sulfides is one of the major causes for the bad breath. A research had been presented (Tonzetich J, Richter V J. Evaluation of volatile odoriferous components of saliva. Arch Oral Biol, 9:39-45, 1964) that either ammonia or sulfide produces more unpleasant odor in mouth by adding whole saliva into different substances. The result of the research showed that mixing whole saliva with compounds containing thiol functional groups (—SH) after 2 hours would produce obvious odor, while it had to take 20 hours for ammonia, formed by mixing whole saliva with nitrides, to produce the noticing unpleasant odor.

When oral bacteria, e.g. Gram-negative, decompose the protein substances with sulfur amino acids, e.g. food debris, saliva, and desquamation of oral epithelium, they produce odorous volatile sulfides: hydrogen sulfide, methyl mercaptan, and dimethyl mercaptan. To effectively eliminate the bad breath, the amount of sulfides in mouth has to be reduced first.

On the other hand, it is known that the main compositions of dental plaque are the inorganic and organic elements in saliva, food debris, and the oral bacteria. If the dental plaque is further calcified, it will produce dental calculus, and lead to periodontal disease. Therefore, in addition to the functions of cleaning mouth and reducing oral odors, it is also important for mouthwash or oral cleaning composition to reduce the amount of harmful oral bacteria to decrease the formation of dental plaque.

U.S. Pat. No. 5,753,217 discloses a method for reducing oral malodor, in which a solution of sodium chlorite and a metal ion is provided as mouth rinse; however, the method can only suppress the bad breath, but not literately eliminate the unpleasant oral odors. In addition, Taiwanese Pat. No. 1305497 provides a dual component dentifrice, which may more effectively eliminate the oral odors than the previous method, but has to add other necessary ingredients, e.g. thickeners, and humectants. As such, not only the manufacturing cost is increased, but also irritation and damage occurs in gums and crowns from chlorine dioxide mixed with the dentifrice.

Therefore, it is the main issue in the art to produce bad breath-eliminating mouthwash in low cost.

SUMMARY

A mouthwash composition is provided, which has antibacterial properties and can eliminate oral odors.

The mouthwash composition comprises water and a modified polyglutamic acid comprised of a plurality of segment A and a plurality of segment B randomly arranged, in which, the segment A has following formula I:

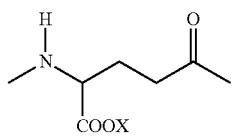

(I)

The segment B has the following formula II:

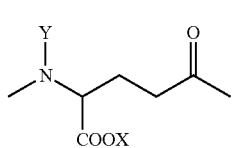

(II)

Wherein X=H, Na, K, $NH_4$, ½Ca, or ½Mg, and Y=Cl, Br, or I. The weight percent of the N—Y haloamine functional group of the segment B in the modified polyglutamic acid is 5-15 wt %, and the concentration of the modified polyglutamic acid in the mouthwash composition is 0.1-5 wt %.

The present invention provides a mouthwash composition, which can eliminate oral odors effectively, and prevent diseases caused by oral bacterial infection, also has low sensitivity to gums, and can be used safely for oral hygiene.

These and other features, aspects, and advantages of the present invention will become better understood with reference to the following description and appended claims.

DETAILED DESCRIPTION

The detailed description provided below is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

A mouthwash composition is provided, which has antibacterial properties and can eliminate bad breath, comprising water and a modified polyglutamic acid comprised of a plurality of segment A and a plurality of segment B randomly arranged, in which, the segment A has following formula I:

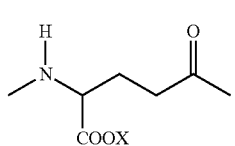

(I)

The segment B has the following formula II:

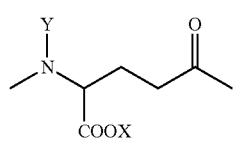

Wherein X=H, Na, K, NH$_4$, ½Ca, or ½Mg, and Y=Cl, Br, or I. The concentration of the modified polyglutamic acid in the mouthwash composition is 0.1-5 wt %.

The modified polyglutamic acid is a polymer composed of a plurality of segment A and a plurality of segment B randomly arranged, wherein there is no specific limitations in the sequence of segment A and segment B. The sequence can be regular, partially regular, irregular, or combination thereof. Specifically, the sequence of segment A and segment B in the modified polyglutamic acid of the present invention, when it is regular, includes but not limited to ABABABAB, AABBAABB, and AAABBAAABB; when it is partially regular, includes but not limited to ABABAAABABB, and AABBAABBABABABB; when it is irregular, includes but not limited to AABABBBAA, and ABBBABABBA. However, the foregoing sequence does not affect the antibacterial properties and the efficacy of eliminating bad breath-causing molecules of the modified polyglutamic acid of the present invention.

The modified polyglutamic acid of the present invention can be prepared in any conventional manner, and there is no limitation in the present invention. For instance, it can be produced by polymerization of segment A and segment B directly or fully by polymerization of segment A producing polyglutamic acid followed by halogenation caused by halogenating agent. The polyglutamic acid produced fully by segment A can be prepared by polymerization of segment A directly, microorganism, isolating from natural materials, or synthesizing by conventional peptide synthesizer.

The treatment of the halogenating agent is not limited in the present invention, e.g. soak, and spray. Use the halogenating agent to oxidize the amine bonds of the segment A to produce modified polyglutamic acid.

The halogenating agent can be applied to the present invention includes, but not limited to perhalic acid, perhalate, halic acid, halate, halous acid, halite, hypohalous acid, hypohalite, halogen gas, trichloroisocyanuric acid (TCCA), and combination thereof. In accordance with one embodiment of the present invention, the halogenating agent is sodium hypochlorite.

The mouthwash composition of the present invention includes a modified polyglutamic acid having a plurality of segment A and a plurality of segment B, wherein the segment B can decompose hydrogen sulfide, which is an unfavorable breath-causing molecule, and reduce the amount of hydrogen sulfide in mouth. In accordance with one embodiment of the present invention, the weight percent of the N—Y haloamine functional group of the segment B in the modified polyglutamic acid is 5-15 wt %. In accordance with another embodiment of the present invention, the weight percent of the N—Y haloamine functional group of the segment B in the modified polyglutamic acid is 10-15 wt %. In accordance with another embodiment of the present invention, the weight percent of the N—Y haloamine functional group of the segment B in the modified polyglutamic acid is 14-15 wt %.

In accordance with one embodiment of the present invention, the concentration of the modified polyglutamic acid in the mouthwash composition is 0.1-5 wt %. Although it can eliminate partial bad breath-causing molecule when the concentration of the modified polyglutamic acid in the mouthwash composition is less than 0.1 wt %, it cannot effectively solve the problem of bad breath. However, the N—Y bond of the modified polyglutamic acid, e.g. N—Cl bond, may react with water and produce hypochlorous acid, and then emit pungent smells of chlorine, and affect the acceptance of users. Therefore, it is better when the concentration of the modified polyglutamic acid in the mouthwash composition is not more than 5 wt %.

The molecular weight of the modified polyglutamic acid is not limited in the present invention. Considering the convenience of operation, in accordance with one embodiment of the present invention, the modified polyglutamic acid has a molecular weight of 500-5,000,000 Daltons; in accordance with another embodiment of the present invention, the modified polyglutamic acid has a molecular weight of 1,000-5,000,000 Daltons.

In order to make the mouthwash composition in the present invention has a better effect of eliminating bad breath, the mouthwash composition has a pH of 6-8 in accordance with one embodiment of the present invention. When the pH is more than 8 or less than 6, though the mouthwash still has effect of eliminating bad breath, it may irritate soft tissue, e.g. cell membrane in mouth, gums.

In order to control the pH of the mouthwash composition and keep it in the foregoing preferred range during use, a pH buffer can be optionally added to the mouthwash composition to control the pH.

The pH buffer is not limited in the present invention, including, but not limited to phosphate buffer, ammonium chloride buffer, acetic acid buffer, sodium hydrogen phosphate buffer, sodium dihydrogen phosphate buffer, benzoic acid buffer, and combination thereof.

The mouthwash composition in the present invention, which can eliminate bad breath, reduces the amount of hydrogen sulfide by the foregoing haloamine functional group. The N—Y haloamine functional group (Y=Cl, Br, or I) in water will undergo slow dissociation caused by water molecules, and release halogen ion that is an oxidizer, then the halogen ion will oxidize the hydrogen sulfide, the hydrogen sulfide will be decomposed and alleviate the problem of bad breath.

The modified polyglutamic acid of the mouthwash composition in the present invention can eliminate bad breath, wherein the halogen ion on the haloamine functional group will be released after dissociation, and depleted after decomposition of hydrogen sulfide; meanwhile, the haloamine functional group will be reduced to N—H amide bond, whereby the modified polyglutamic acid would become conventional polypeptide compound. The peptide bonds of the polypeptide compound will be breakdown by microorganisms and fungi, then degraded to ammonia, carbon dioxide, and water that are harmless to environment in the end.

The detailed description provided below is intended as a description of the present examples and is not intended to represent the only forms in which the present example may be constructed or utilized. Therefore, the spirit and scope of the appended claims should not be limited to the description of the embodiments contained herein.

Embodiment

Measuring the Concentration of the N—Cl Haloamine Functional Group

The concentration of the N—Cl haloamine functional group was measured by titration comprising the steps of:
1. 5 g of sodium sulfate (Aldrich, US) was diluted with pure water to 200 mL as sodium thiosulfate titrant.
2. 0.5 g of polymer to be tested was weighed, then 1 g of potassium iodide powder (Aldrich, US) and 40 mL of pure water were added, and the solution was continually stirred until the powder dissolved in the solution. Small amount of acetic acid was added as catalyst when necessary.
3. The solution of Step 2 was used as the analyte, the sodium thiosulfate of Step 1 as the titrant, and starch solution (Aldrich, US) as the indicator. The endpoint of the titration was indicated by the color of the solution turning brown to colorless. The volume of used sodium thiosulfate titrant was recorded.
4. The equation of titration was as following (a):

$$NCl + 2I^- + H^+ \rightarrow Cl^- + NH + I_2$$

$$I_2 + 2S_2O_3^{2-} \rightarrow 2I^- + S_4O_6^{2-} \quad (a)$$

According to the equation (a), the amount of the N—Cl haloamine functional group in the polymer per gram could be known by the moles of used sodium thiosulfate titrant.

Preparing Different Weight Percent of Segment B in Modified Polyglutamic Acid

Embodiment 1

10.0 g of polyglutamic acid (molecular weight is about 2,000,000, Vedan, Taiwan) was put into a 250 mL flask, and dissolved by adding 90 mL of pure water to obtain a polyglutamic acid solution. Then, 4 g of sodium hypochlorite solution was added, which the concentration was 12.65 wt %, to obtain a mixture. The mixture was continually stirred at room temperature for 30 minutes making polyglutamic acid react with sodium hypochlorite. The reacted mixture was put into a separatory funnel and isopropanol was used to separate out polymer 1 followed by drying in a vacuum drying oven. The product after drying was white to pale yellow powder, which was water-soluble. The weight percent of the N—Cl haloamine functional group in modified polyglutamic acid was measured by titration using polymer 1 as the analyte and sodium thiosulfate as the titrant.

Embodiment 2-6

As described in embodiment 1, but 12, 20, 28, 36, and 40 g of sodium hypochlorite solutions were added to polyglutamic acid solution respectively. The mixtures were continually stirred at room temperature for 30 minutes making polyglutamic acid react with sodium hypochlorite. The reacted mixtures were put into separatory funnels respectively and isopropanol was used to separate out polymer 2-6 followed by drying in a vacuum drying oven. The products after drying were white to pale yellow powder, which were water-soluble. The weight percents of the N—Cl haloamine functional group in modified polyglutamic acid were measured by titration using polymer 2-6 as the analytes and sodium thiosulfate as the titrant.

Embodiment 7-8

As described in embodiment 1, but the stirring time of the mixtures at room temperature were extended to 90 and 180 minutes respectively. After stirring, the reacted mixtures were added into separatory funnels respectively and isopropanol was used to separate out polymer 7 and 8 followed by drying in a vacuum drying oven. The products after drying were white to pale yellow powder, which were water-soluble. The weight percents of the N—Cl haloamine functional group in modified polyglutamic acid were measured by titration using polymer 7 and 8 as the analytes and sodium thiosulfate as the titrant.

Comparative Example 10 g of untreated polyglutamic acid C1 was used as a control.

Table 1 showed the condition of reagents, reaction time, and the result of weight percent of the N—Cl haloamine functional group in modified polyglutamic acid.

TABLE 1

| Polymer | Polyglutamic acid (g) | Sodium hypochlorite solution (g) | Sodium hypochlorite (g) | Reaction time (min) | Weight percent of the N—Cl haloamine functional group in modified polyglutamic acid (wt %) |
|---|---|---|---|---|---|
| C1 | 10 | 0 | 0 | 0 | 0 |
| 1 | 10 | 4 | 0.51 | 30 | 2.32 |
| 2 | 10 | 12 | 1.52 | 30 | 3.80 |
| 3 | 10 | 20 | 2.53 | 30 | 5.78 |
| 4 | 10 | 28 | 3.54 | 30 | 8.28 |
| 5 | 10 | 36 | 4.55 | 30 | 10.93 |
| 6 | 10 | 40 | 5.06 | 30 | 11.00 |
| 7 | 10 | 40 | 5.06 | 90 | 14.61 |
| 8 | 10 | 40 | 5.06 | 180 | 13.41 |

Antibacterial Test

Most antibacterial tests of antibacterial were evaluated by against wide range of microorganisms, including Gram-positive and Gram-negative bacteria. *Staphylococcus aureus* (BCRC Number 15211) and *Escherichia coli* (BCRC Number 11446) were used as test brothes in the present invention. Wherein, the *Staphylococcus aureus* is Gram-positive and *Escherichia coli* is Gram-negative.

A. Antibacterial Qualitative Test

100 μL of test brothes of *Staphylococcus aureus* and *Escherichia coli* were inoculated, which concentrations were both $10^6$-$10^7$ CFU/mL, on different agar plates respectively, and spread evenly by triangle glass rod. Polymer 1-8 and polymer C1 were made into discs, and the discs were placed horizontally on the agar plates with test brothes respectively, then the agar plates were incubated in an incubator at 37. After incubating for 14-24 hours, the discs and surroundings of the discs were observe. It was obvious and can be seen with the naked eye that there were no colonies formed on the surfaces of the discs and their surroundings of polymer 1-8, while there were colonies formed on the surface of the disc and its surroundings of polymer C1.

B. Antibacterial Quantitative Test

The test was based on the antimicrobial benchmark of ASTM E2149. The foregoing test brothes (*Staphylococcus aureus* and *Escherichia coli*) were diluted 10 times, whereby the concentrations would be adjusted to $10^5$-$10^6$ CFU/mL as the test brothes for the present test.

125 mg of polymer 1-8 were weighed and 125 mg of polymer C1 was used as a control, and 5 mL of test broth was inoculated to incubate. After incubating for 24 hours, the numbers of colonies of polymer 1-8 and polymer C1 without incubating (P) and the numbers of colonies of polymer 1-8 and polymer C1 after incubating (Q) were determined. The antibacterial activity was calculated by following equation (b):

$$\text{Antibacterial activity} = \frac{(P-Q)}{P} \times 100\% \quad (b)$$

Wherein, P represented the number of colonies after inoculating test broth but not incubating, while Q represented the number of colonies after inoculating test broth and incubating for 24 hours. When Q was far greater than P, it meant that the polymer did not have antibacterial activity. The antibacterial activity of polymer 1-8 and control polymer C1 were presented in Table 2 and Table 3.

TABLE 2

The antibacterial activity using *Staphylococcus aureus* as test broth (ASTM E 2149 as benchmark)

| Polymer | Colony density (CFU/cm²) 0 hour | 24 hours | Antibacterial activity (%) |
|---|---|---|---|
| C1 | $3.65 \times 10^5$ | $7.97 \times 10^7$ | 0 |
| 1 | $3.51 \times 10^5$ | 0 | >99.9 |
| 2 | $2.98 \times 10^5$ | 0 | >99.9 |
| 3 | $3.44 \times 10^5$ | 0 | >99.9 |
| 4 | $2.89 \times 10^5$ | 0 | >99.9 |
| 5 | $3.82 \times 10^5$ | 0 | >99.9 |
| 6 | $3.36 \times 10^5$ | 0 | >99.9 |
| 7 | $3.51 \times 10^5$ | 0 | >99.9 |
| 8 | $3.73 \times 10^5$ | 0 | >99.9 |

TABLE 3

The antibacterial activity using *Escherichia coli* as test broth (ASTM E 2149 as benchmark)

| Polymer | Colony density (CFU/cm²) 0 hour | 24 hours | Antibacterial activity (%) |
|---|---|---|---|
| C1 | $2.82 \times 10^5$ | $6.50 \times 10^7$ | 0 |
| 1 | $3.13 \times 10^5$ | 0 | >99.9 |
| 2 | $3.44 \times 10^5$ | 0 | >99.9 |
| 3 | $3.57 \times 10^5$ | 0 | >99.9 |
| 4 | $3.46 \times 10^5$ | 0 | >99.9 |
| 5 | $3.22 \times 10^5$ | 0 | >99.9 |
| 6 | $3.61 \times 10^5$ | 0 | >99.9 |
| 7 | $3.37 \times 10^5$ | 0 | >99.9 |
| 8 | $3.76 \times 10^5$ | 0 | >99.9 |

C. Antibacterial Quantitative Test

The test was based on the antimicrobial benchmark of AATCC 100. Cotton were impregnated with polymer 1-8 and polymer C1 and cut into 2×2 cm² square test strips respectively, then each test strip was placed horizontally on the bottom of a 50 mL serum bottle, and 20 µL of test broth (*Staphylococcus aureus* and *Escherichia coli*) with the concentration of $10^6$-$10^7$ CFU/mL was inoculated. After the test strip was contacted with the test broth, the test strip was rinsed with 20 mL of sterile water promptly, and the number of colonies without incubating (P) was determined. Another group of inoculated square test strips, after the test strips were contacted with the test broth, were incubated for 24 hours and the numbers of colonies after incubating (Q) were determined.

The antibacterial activity can be determined by the foregoing equation (b). The antibacterial activity of polymer 1-8 and control polymer C1 were presented in Table 4 and Table 5, and the colony density (CFU/cm²) in Table 4 and Table 5 was the number of colonies on the 2×2 cm² test strip divided by the area of the test strip.

TABLE 4

The antibacterial activity using *Staphylococcus aureus* as test broth (AATCC 100 as benchmark)

| Polymer | Colony density (CFU/cm²) 0 hour | 24 hours | Antibacterial activity (%) |
|---|---|---|---|
| C1 | $6.95 \times 10^5$ | $8.55 \times 10^7$ | 0 |
| 1 | $7.03 \times 10^5$ | 0 | >99.9 |
| 2 | $6.14 \times 10^5$ | 0 | >99.9 |
| 3 | $6.63 \times 10^5$ | 0 | >99.9 |
| 4 | $7.16 \times 10^5$ | 0 | >99.9 |
| 5 | $5.22 \times 10^5$ | 0 | >99.9 |
| 6 | $5.61 \times 10^5$ | 0 | >99.9 |
| 7 | $6.37 \times 10^5$ | 0 | >99.9 |
| 8 | $6.76 \times 10^5$ | 0 | >99.9 |

TABLE 5

The antibacterial activity using *Escherichia coli* as test broth (AATCC 100 as benchmark)

| Polymer | Colony density (CFU/cm²) 0 hour | 24 hours | Antibacterial activity (%) |
|---|---|---|---|
| C1 | $5.82 \times 10^5$ | $7.53 \times 10^7$ | 0 |
| 1 | $6.13 \times 10^5$ | 0 | >99.9 |
| 2 | $5.24 \times 10^5$ | 0 | >99.9 |
| 3 | $5.57 \times 10^5$ | 0 | >99.9 |
| 4 | $5.75 \times 10^5$ | 0 | >99.9 |
| 5 | $7.64 \times 10^5$ | 0 | >99.9 |
| 6 | $6.83 \times 10^5$ | 0 | >99.9 |
| 7 | $7.05 \times 10^5$ | 0 | >99.9 |
| 8 | $5.96 \times 10^5$ | 0 | >99.9 |

According to Table 2, 3, 4 and 5, the biodegradable polymer 1-8 of the present invention had good antibacterial activity to Gram-positive and Gram-negative bacteria.

Evaluating Effect of Eliminating Bad Breath-Causing Molecule

The present test used hydrogen sulfide, which is the major element causing bad breath, as the object of evaluation. Gas chromatograph was used to detect the concentration change of hydrogen sulfide and analyze the ability of modified polyglutamic acid for decomposing hydrogen sulfide.

D. Preparing Standard Hydrogen Sulfide Gas and Setting the Calibration Curve

The preparation of standard gas was a dynamic dilution system, and the major components included a standard gas cylinder with 5 ppm hydrogen sulfide, a source of compressed air, a gas filter device, a bi-directional gas switching valve, a mass flow controller, a humidification bottle, a buffer bottle, a wet and dry air mixing chamber, a test gas mixing chamber, and a pressure regulator. The 5 ppm hydrogen sulfide standard gas was diluted to 2.5 ppm, 1 ppm, and 0.3 ppm using different velocities of flow. Then, the 5 ppm, 2.5 ppm, 1 ppm, and 0.3 ppm hydrogen sulfide gas were sampled and analyzed, and the software in the gas chromatograph was used to establish a calibration curve of gas concentration and logarithm of peak area. The concentration of hydrogen sulfide gas (C) was obtained by the following equation:

$$C = \frac{C_s P_s V_s (273 + t_m)}{P_m V_m (273 + t_s)}$$

$C_s$: Concentration of compound obtained by the calibration curve (ppm)
$P_s$: Atmospheric pressure when the calibration cure was prepared (mmHg)
$V_s$: Volume of standard gas (L)
$P_m$: Atmospheric pressure when sampling (mmHg)
$V_m$: Volume of sample (L)
$t_s$: Atmospheric temperature when the calibration cure was prepared (° C.)
$t_m$: Atmospheric temperature when sampling (° C.)

E. Evaluating the Ability of Modified Polyglutamic Acid to Discompose Hydrogen Sulfide 50 mL solutions of polymer 1, 3, 4, 5, and 7 with concentration of 0.1 wt % were prepared, added to gas sampling bags containing 3 L of 5 ppm hydrogen sulfide standard gas. After vigorous gas-liquid mixing for 30 and 120 seconds respectively, the concentrations of hydrogen sulfide were detected and analyzed.

In addition, deionized water was added to gas sampling bag containing hydrogen sulfide standard gas as Control 1, and no water or solution was added to gas sampling bag, which was pure hydrogen sulfide, as Control 2.

Furthermore, commercially available mouthwash (Want Want, Taiwan, Model: Watergod) was mixed with hydrogen sulfide standard gas for 30 seconds, 3 tests was repeated as Control 3, Control 4, and Control 5 respectively, the concentrations of hydrogen sulfide were detected and analyzed.

TABLE 6

The concentration change after mixing hydrogen sulfide and modified polyglutamic acid for 30 seconds

| Reactant mixed with hydrogen sulfide standard gas | Concentration of hydrogen sulfide (ppm) |
|---|---|
| Control 1 | 4.96 |
| Control 2 | 4.88 |
| Control 3 | 4.53 |
| Control 4 | 4.48 |
| Control 5 | 4.36 |
| Polymer 1 | 4.66 |
| Polymer 1 | 4.75 |
| Polymer 1 | 4.69 |
| Polymer 3 | 4.29 |
| Polymer 3 | 4.18 |
| Polymer 3 | 4.24 |
| Polymer 4 | 4.09 |
| Polymer 4 | 4.15 |
| Polymer 4 | 4.12 |
| Polymer 5 | 3.56 |
| Polymer 5 | 3.46 |
| Polymer 5 | 3.52 |
| Polymer 7 | 3.25 |
| Polymer 7 | 3.20 |
| Polymer 7 | 3.18 |

TABLE 7

The concentration change after mixing hydrogen sulfide and modified polyglutamic acid for 120 seconds

| Reactant mixed with hydrogen sulfide standard gas | Concentration of hydrogen sulfide (ppm) |
|---|---|
| Control 1 | 4.96 |
| Control 2 | 4.78 |
| Polymer 1 | 4.51 |
| Polymer 1 | 4.46 |
| Polymer 1 | 4.58 |
| Polymer 3 | 3.66 |
| Polymer 3 | 3.95 |
| Polymer 3 | 3.89 |
| Polymer 4 | 3.22 |
| Polymer 4 | 3.19 |
| Polymer 4 | 3.29 |
| Polymer 5 | 3.09 |
| Polymer 5 | 3.05 |
| Polymer 5 | 3.06 |
| Polymer 7 | 2.92 |
| Polymer 7 | 2.86 |
| Polymer 7 | 2.78 |

According to Table 6 and Table 7, the modified polyglutamic acid in the present invention can reduce the concentration of bad breath-causing molecule, hydrogen sulfide. Wherein, polymer 3, 4, 5, and 7 (The weight percents of N—Cl haloamine functional groups in modified polyglutamic acid were 5.78 wt %, 8.28 wt %, 10.93 wt %, and 14.61 wt % respectively), comparing to commercially available mouthwash, can effectively reduce concentration of bad breath-causing molecule and eliminate bad breath.

F. Evaluating the Ability of Different Concentrations of Modified Polyglutamic Acid Solutions to Discompose Hydrogen Sulfide Generally, the duration of using mouthwash was 30-120 seconds, and polymer 7 was used to prepare 50 mL of solutions with the concentration of 0.01 wt %, 0.1 wt %, 0.5 wt %, 2 wt %, and 5 wt % respectively in the present test. The polymer solutions were added to gas sampling bags containing 3 L of 5 ppm hydrogen sulfide standard gas. After vigorous gas-liquid mixing for 30, 60, and 120 seconds, the concentrations of hydrogen sulfide were detected and analyzed. In addition, deionized water was added to gas sampling bag containing hydrogen sulfide standard gas as Control 1, and no water or solution was added to gas sampling bag, which was pure hydrogen sulfide, as Control 2.

Furthermore, commercially available mouthwash (Want Want, Taiwan, Model: Watergod) was mixed with hydrogen sulfide standard gas for 30, 60, and 120 seconds, 3 tests were repeated as Control 3, Control 4, and Control 5 respectively, and the concentrations of hydrogen sulfide were detected and analyzed.

TABLE 8

The concentration of hydrogen sulfide after gas-liquid mixing for 30 seconds

| Concentration of modified polyglutamic acid (wt %) | Concentration of hydrogen sulfide (ppm) |
|---|---|
| Control 1 | 4.96 |
| Control 2 | 4.88 |
| Control 3 | 4.53 |
| Control 4 | 4.48 |
| Control 5 | 4.36 |
| 0.01 | 4.25 |
| 0.01 | 4.31 |
| 0.01 | 4.28 |
| 0.1 | 3.25 |
| 0.1 | 3.20 |
| 0.1 | 3.18 |
| 0.5 | 2.18 |
| 0.5 | 2.22 |
| 0.5 | 2.15 |
| 2.0 | 1.60 |
| 2.0 | 1.55 |
| 2.0 | 1.62 |
| 5.0 | 1.23 |
| 5.0 | 1.19 |
| 5.0 | 1.18 |

TABLE 9

The concentration of hydrogen sulfide after gas-liquid mixing for 60 seconds

| Concentration of modified polyglutamic acid (wt %) | Concentration of hydrogen sulfide (ppm) |
|---|---|
| Control 1 | 4.96 |
| Control 2 | 4.83 |
| Control 3 | 4.28 |
| Control 4 | 4.31 |
| Control 5 | 4.35 |
| 0.01 | 4.12 |
| 0.01 | 4.20 |
| 0.01 | 4.16 |
| 0.1 | 3.12 |
| 0.1 | 3.09 |
| 0.1 | 3.05 |
| 0.5 | 1.78 |
| 0.5 | 1.82 |
| 0.5 | 1.75 |
| 2.0 | 1.30 |
| 2.0 | 1.22 |
| 2.0 | 1.26 |
| 5.0 | 0.89 |
| 5.0 | 0.92 |
| 5.0 | 0.98 |

TABLE 10

The concentration of hydrogen sulfide after gas-liquid mixing for 120 seconds

| Concentration of modified polyglutamic acid (wt %) | Concentration of hydrogen sulfide (ppm) |
|---|---|
| Control 1 | 4.96 |
| Control 2 | 4.78 |
| Control 3 | 4.06 |
| Control 4 | 3.98 |
| Control 5 | 3.95 |
| 0.01 | 4.02 |
| 0.01 | 4.10 |
| 0.01 | 4.06 |
| 0.1 | 2.92 |
| 0.1 | 2.86 |
| 0.1 | 2.78 |
| 0.5 | 1.52 |
| 0.5 | 1.48 |
| 0.5 | 1.56 |
| 2.0 | 1.09 |
| 2.0 | 1.16 |
| 2.0 | 0.96 |
| 5.0 | 0.62 |
| 5.0 | 0.78 |
| 5.0 | 0.68 |

According to Table 8, 9, and 10, the modified polyglutamic acid of the present invention can effectively reduce the amount of bad breath-causing molecule, hydrogen sulfide, and improve problems caused by bad breath.

A mouthwash composition is provided, wherein the modified polyglutamic acid decomposes hydrogen sulfide, the major element causing bad breath, by redox to eliminate oral odors and solve the problem of bad breath effectively. Moreover, the mouthwash composition has good antibacterial properties, can suppress the formation of dental plaque and prevent the inflammation of gums or the occurrence of periodontal disease.

The mouthwash composition of the present invention can eliminate oral odors effectively, and prevent diseases caused by oral bacterial infection, also has low sensitivity to gums, and can be used safely for oral hygiene.

Although embodiments of the present disclosure and their advantages have been described in detail, they are not used to limit the present disclosure. It should be understood that various changes, substitutions and alterations could be made herein without departing from the spirit and scope of the present disclosure. Therefore, the protecting scope of the present disclosure should be defined as the following claims.

What is claimed is:

1. A method for the reducing amount of molecules causing bad breath, comprising:
providing a mouthwash composition;
adding the mouthwash composition into an oral cavity containing molecules causing bad breath, said molecules including hydrogen sulfide; and
mixing the mouthwash composition and the molecules causing bad breath,
wherein the mouthwash composition comprises water and a modified polyglutamic acid composed of a plurality of segment A and a plurality of segment B randomly arranged, wherein the segment A has a formula I:

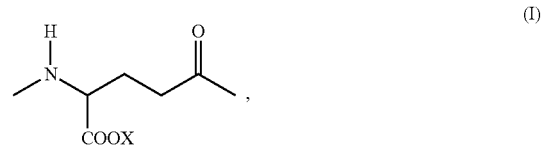

the segment B has a formula II:

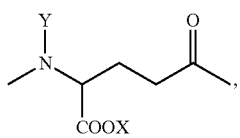

(II)

wherein X=H, Na, K, NH₄, ½Ca, or ½Mg, Y=Cl, Br, or I, and the modified polyglutamic acid in said mouthwash composition is present in an amount of 0.1-5 wt %.

2. The method of claim 1, wherein the mixing step has a duration of not less than 30 seconds.

3. The method of claim 2, wherein the mixing step has a duration of 30-120 seconds.

4. The method of claim 1, wherein the N—Y haloamine functional group of the segment B in the modified polyglutamic acid is present in an amount of 5-15 wt %.

5. The method of claim 1, wherein the N—Y haloamine functional group of the segment B in the modified polyglutamic acid is present in an amount of 10-15 wt %.

6. The method of claim 1, wherein the N—Y haloamine functional group of the segment B in the modified polyglutamic acid is present in an amount of 14-15 wt %.

7. The method of claim 1, wherein the modified polyglutamic acid has a molecular weight of 500-5,000,000 Daltons.

8. The method of claim 1, wherein the modified polyglutamic acid has a molecular weight of 1,000-5,000,000 Daltons.

9. The method of claim 1, wherein the composition has a pH of 6-8.

10. The method of claim 1, wherein the composition further comprises a pH buffer.

11. The method of claim 10, wherein the pH buffer is selected from the group consisting of a phosphate buffer, a sodium hydrogen phosphate buffer, a sodium dihydrogen phosphate buffer, and combinations thereof.

* * * * *